United States Patent [19]

Hennessy et al.

[11] Patent Number: 4,706,207

[45] Date of Patent: Nov. 10, 1987

[54] COUNT ACCURACY CONTROL MEANS FOR A BLOOD ANALYSES SYSTEM

[75] Inventors: James W. Hennessy, Trumbull; Henry R. Angel, Fairfield; Richard A. Carlson, Meriden, all of Conn.

[73] Assignee: Nova Celltrak, Inc., Trumbull, Conn.

[21] Appl. No.: 748,003

[22] Filed: Jun. 24, 1985

[51] Int. Cl.[4] ................... G01N 15/12; G01N 33/48; G06M 11/04
[52] U.S. Cl. .................................. 364/555; 356/39; 364/416
[58] Field of Search ............... 364/414, 415, 416, 555; 356/39, 40, 414

[56] References Cited

U.S. PATENT DOCUMENTS

| | | | |
|---|---|---|---|
| 3,874,850 | 4/1975 | Sorensen et al. | 356/40 X |
| 4,030,888 | 6/1977 | Yamamoto et al. | 356/39 X |
| 4,071,891 | 1/1978 | Barrows | 364/555 X |
| 4,128,884 | 12/1978 | England | 364/555 X |
| 4,206,504 | 6/1980 | Frey | 364/416 |
| 4,274,744 | 6/1981 | Chae et al. | 356/414 |
| 4,412,175 | 10/1983 | Maynarez | 364/555 X |
| 4,488,248 | 12/1984 | Okada et al. | 364/555 |

Primary Examiner—Felix D. Gruber
Attorney, Agent, or Firm—Dann, Dorfman, Herrell & Skillman

[57] ABSTRACT

An apparatus for making blood counts is provided with computer and instrument control to optimize performance of the apparatus. Means for counting blood cells such as platelets, white blood and red blood cells enables a plot of the number of particles counted in each of the adjacent bands or channels inclusive within a selected range of particle size so that a plot of count against particle size may be made. The computer enables analyses of plots thus obtained by system algorithms in order to correct errors of various types which may occur in the plot. For example, by calculating the logarithms of the counts of particles and of mean particle size for each particle size channel, a further plot of log count against log of blood particle size of generally symmetrical bell shape may be generated. The computer further calculates change of logarithm ($\Delta$ log) of counts in adjacent channels. A straight line of fixed slope is then plotted representing the change of logarithm of counts against the logarithm of blood particle size, giving more weight to those points near the peak. The calculation steps are reversed using the points on the straight line for ultimately calculating counts in the various channels from $\Delta$ log and taking the anti-log of the log particle size to regenerate a new curve showing more accurately distribution of the selected blood particles against particle size.

14 Claims, 15 Drawing Figures

CELLTRAK-2200

___CBC  RBC/PLT_____WBC/HGB___PRP___DIFF
REQ'D BY_____ DATE_____
DATE 11/08/84    TIME: 07:55
ID #000001
WBC  6.3 THOU
RBC  4.30 MIL
HGB  13.0 g/dl
HCT  39.0 %
MCV  90.0 %
MCH  30.2%
MCHC 33.3%
PLT  260. THOU
TCT  .24%
MPV  9.10 fl

```
 2    10      20       30   PLT (fl)
```

DIFFERENTIAL         MORPHOLOGY
Seg   ___%  ____Thou  Polychrom  ___
Band  ___%  ____Thou  Hypochrom  ___
Lymph ___%  ____Thou  Poik       ___
Mono  ___%  ____Thou  Target     ___
Eosin ___%  ____Thou  Sphero     ___
Baso  ___%  ____Thou  Aniso      ___
Atyp                  Micro      ___
Lymph ___%  ____Thou  Macro      ___
----- ___%  ____Thou  Basco Stip ___
----- ___%  ____Thou  Vacuoles   ___
----- ___%  ____Thou  Toxic Gran ___
nRBC  ___%            PLT        ___

FIG. 9

COUNT ACCURACY CONTROL MEANS FOR A BLOOD ANALYSES SYSTEM

FIELD OF THE INVENTION

The present invention relates to a system and subsystems for controlling an instrument for automatically analyzing blood. The system includes means for calibrating the instrument, controlling the sequence and operation of its parts and automatically displaying instructions in connection with the controlling of the system and test results. More specifically, the present invention relates to means for computer control of calibration, operation and related functions of a hematology system such as that taught in U.S. patent application Ser. No. 675,378, filed Nov. 27, 1984, and assigned to Angel Engineering Corporation, the assignee of the present invention.

BACKGROUND OF THE INVENTION

What is known about the prior art has more to do with the structure described in application Ser. No. 675,378 and, therefore, has been stated in that application. The present invention relating to control functions and computer control applies to the field more broadly than merely use in the system or apparatus of application Ser. No. 675,378. It is believed to provide some completely new approaches in the blood analysis field.

SUMMARY OF THE INVENTION

The aforesaid hematology system of U.S. patent application Ser. No. 675,378 permits automatic handling of most blood tests. This system provides the apparatus for accomplishing blood analysis and the specification describes how the apparatus functions. The present invention relates to the computer control which was not specifically described or shown but the possibility of whose presence could be inferred through the input and output apparatus of the total instrument disclosed.

The present invention relates to a computer controlled system which may employ a microprocessor of known type which functions to control the various operational functions and sequences of the apparatus. For example, it controls the aspiration and the discharge of diluent into the system. It controls the positioning of the movable valve, which is preferably a multi-position rotary valve, into the precise operating positions required for each of the operational steps of any test. The computer also controls cleaning of the passages of the movable valve, cleaning the vacutainer input chamber and the aspirator tip compartment and such other maintenance functions as may be required. The movable valve may also have its parts manually or automatically separated for manual cleaning as described in application Serial No. 675,378.

The system also sees to calibration and the numerical accuracy in calibration. It is provided with security in the form of an access code. The system permits changes both of the security access code and of calibration, in both cases either at the system or from a remote location, and it provides an automatic remote station inquiry technique for obtaining information from the manufacturer for properly performing various tests. After the tests have been performed, it calculates various parameters needed for output. It outputs them on a display and issues a printed ticket showing the results of the test.

The hematology system of the present invention provides a system capable of quantitative determination of the following: a white blood cell count (WBC); a red blood cell count (RBC); hemoglobin (HGB); mean corpuscular volume (MCV); platelet count (PLT); and mean platelet volume (MPV). The system is also capable of calculating from test results of the RBC, HGB, MCV, PLT and MPV the following: hematocrit (HCT); mean corpuscular hemoglobin (MCH); mean corpuscular hemoglobin concentration (MCHC); and thrombocrit (TCT).

DESCRIPTION OF A PREFERRED EMBODIMENT OF THE INVENTION

For a better understanding of the present invention, reference is made to the accompanying drawings in which:

FIG. 9 is a typical print out by the printer of the present invention; and

The hematology system of the present invention provides controls for apparatus described in U.S. application Ser. No. 675,378, providing an automated microprocessor based benchtop, multiparameter hematology instrument. The system consists of the analyzer or microprocessor, a printer, a differential counter, supplies various reagents and consumables and the fluid system for automatically handling the blood samples. The complete system requires a total work area of approximately four feet by two feet.

The throughput of the system is approximately 60 specimens per hour. The displays and indicators on the screen output will provide the operator with information concerning the status of every test and will aid the operator in normal operation, or calibration, or will prompt to alert the operator to troubleshoot problems such as clogs and overrange. The modular construction makes for easy servicing.

Figure 1:
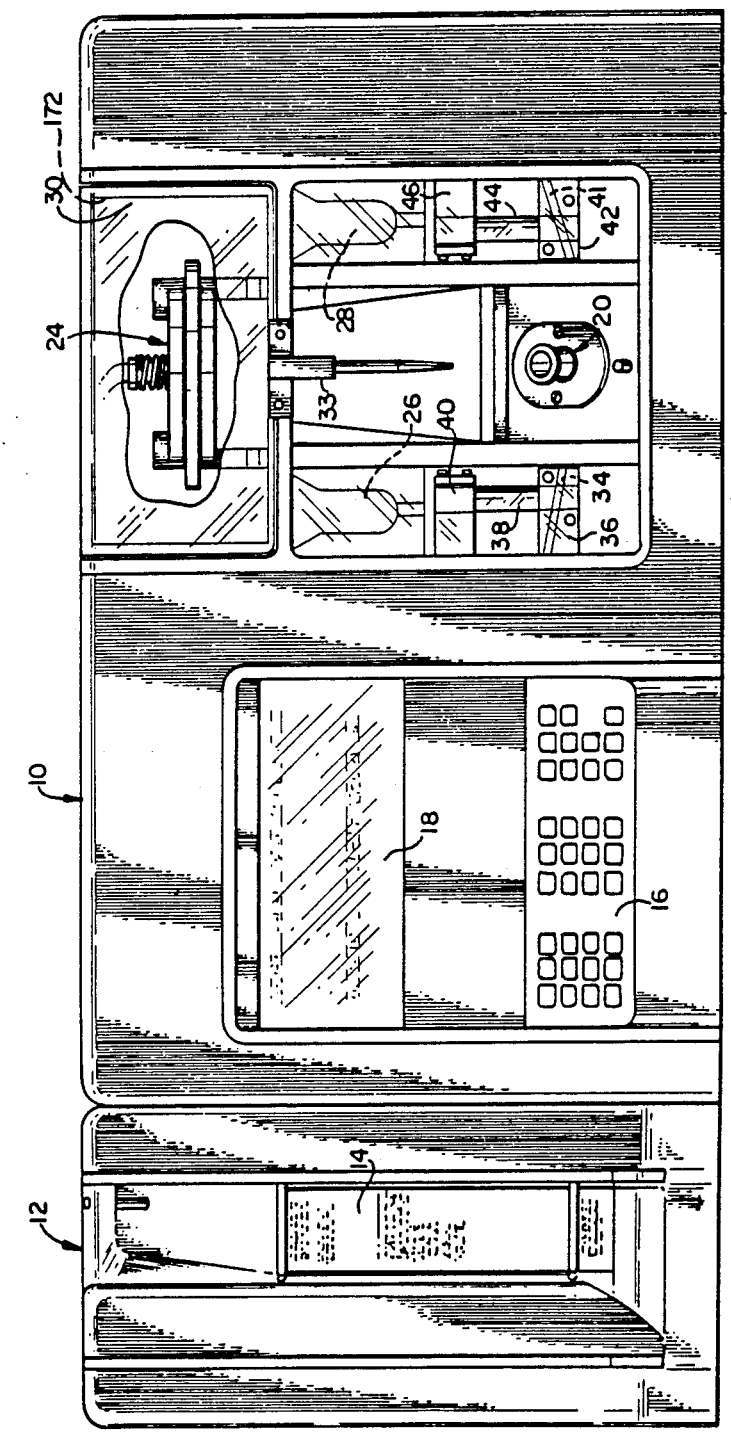
FIG. 1 is an elevational view from the front of a proposed apparatus in accordance with the present invention.

Referring first to FIG. 1, there is illustrated a preferred blood analysis apparatus in accordance with the present invention, housed within two adjacent housings 10 and 12. Housing 10 encloses and supports the mechanical and fluid handling portions of the system as well as input control and display functions. Add on cabinet 12 houses a printer responsive to data generated by the computer within cabinet 10 to print out on slips 14 a hard copy of the blood test results. Input information, such as the nature of a blood test required, is input to the system through keyboard 16 to the internal computer and electronic system. To make some white blood counts, a cytologist making a visual count may need a differential input 15 to manually introduce counts as they are made. A module with a plug-in connection through housing 10, may be added permitting input from differential keyboard 17. Although not suggested by the drawing, the connecting cord should be sufficiently long to permit movement from place to place, such as to microscope and desk locations. Output of test information is displayed on alpha numeric display 18, and may be printed out on slips 14 if the printer in housing 12 is employed.

Blood samples may be handled automatically either with open or sealed vacuum containers. Vacuum containers are inserted into receptacle 20 with their resilient closure down for automatic puncture and removal of blood samples. Samples from open containers are fed into the system through aspirator 22. The system has at its heart a rotary valve 24 which is repositioned for various steps in the automatic handling of the blood sample including a dilution step by which blood properly diluted for a red blood count is placed into container 26. A properly diluted sample for a white blood count is placed in container 28. These containers are open and accessible from above when the hinged transparent cover 30 conforming to the shape of the front and top of the housing is open. Cover 30 rotates about a hinge at its top edge to expose valve 24 for maintenance and repairs. Raising cover 30 also allows hand diluted samples to be added to the containers 26 and 28 from above.

A start switch lever 33 is also provided just below the cover. The start switch is actuated to enable the system to begin its sequence of test steps.

Properly diluted red blood samples are fed by suitable tubular connection from container 26 to the counter portion. The counter container consists of a passage 34 in block 36 generally tangent to a jewel orifice of great precision in the sidewall of vertically oriented tube 38. Tube 38, in turn, is supported by a bracket 40. Similarly, white blood counts are made by passing the diluted and lysed white blood sample from container 28 by suitable tubing connection through passage 140 into block 42 so that it passes tangent to tube 44 whose sidewall contains a jewel orifice of suitably different dimensions. Tube 44 and support block 42 are supported on the housing by bracket 46.

Figure 2:
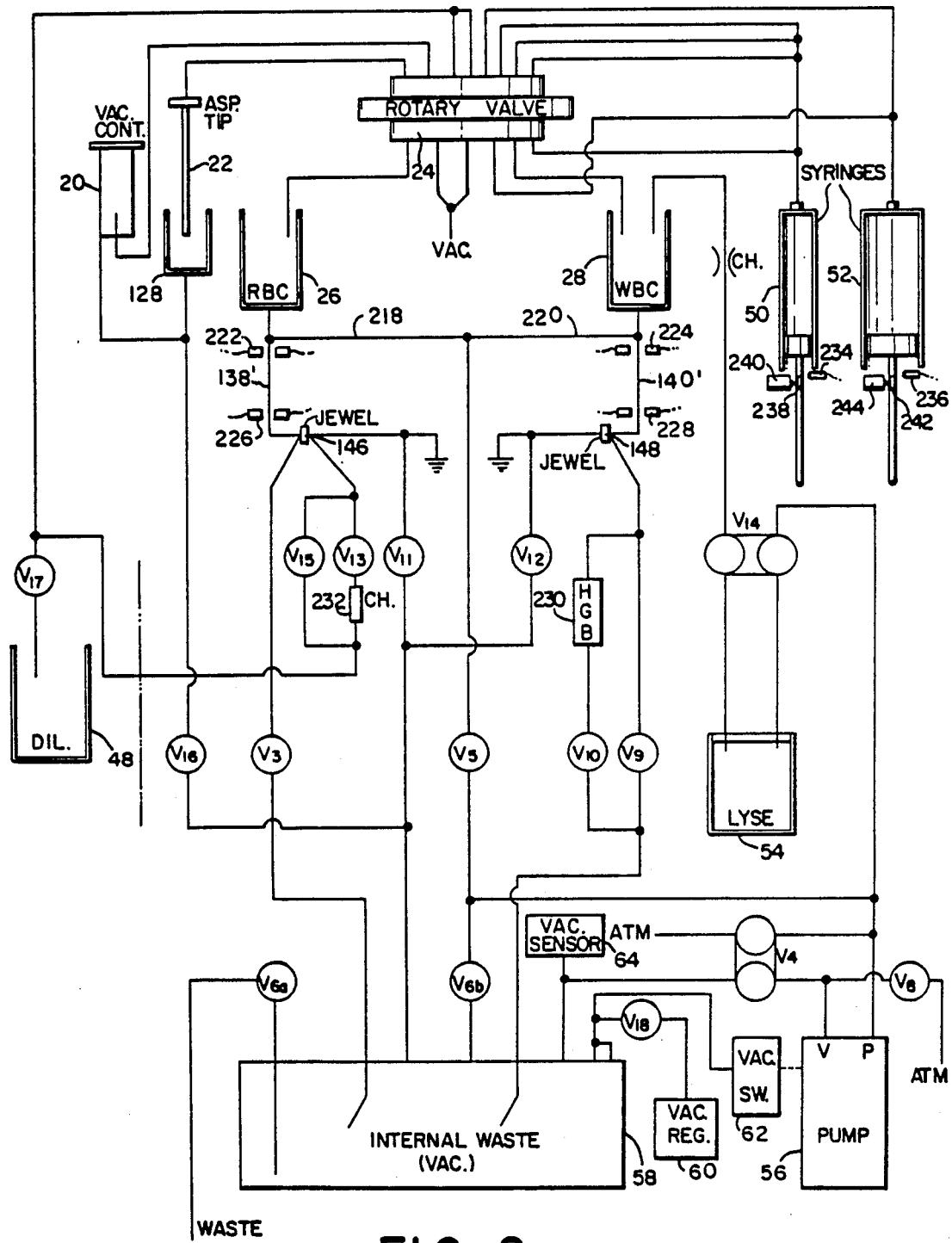
FIG. 2 is a schematic diagram showing the flow and control of fluids through the device.
Figure 4:
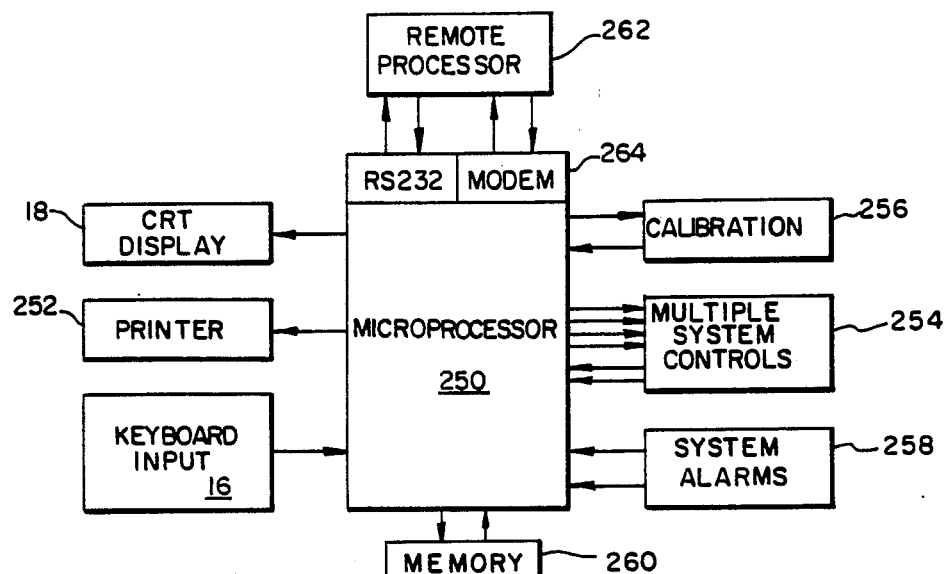
FIG. 4 is a block diagram showing schematically the broad interrelationships of components affected by or affecting the computer.

It will be appreciated that internally of the housing 10 there are located a great many necessary fluid system components which are considered in connection with FIG. 2 and lines as well as the computer, counter, processing means, input circuitry, and the like, which are generally considered in connection with FIG. 4 and which, while conventional as components, are provided in a new combination to provide an automatic, or semi automatic, computer controlled blood test apparatus.

The principle parts of the fluid system are shown schematically in FIG. 2. FIG. 2 contains components, or parts related to the components already disclosed, as well as such additional components as are needed to complete the fluid system. It will be understood that the single lines shown, are intended to represent tubing or pipe which, in some cases, is flexible. No effort has been made, nor needs to be made, to explain conventional connections between such tubing or pipe and various components.

Input into the system is preferably through the aspirator tip 22 which draws blood from a container which is open, or, from a vacuum container inserted into the vacuum container input structure 20. In either case, input is through a multi-position slide valve, preferably a rotary valve 24, whose positioning is determined by what stage of the process is involved. In this connection. it should be noted that the lines shown as input to the rotary valve in FIG. 2 are, indeed, merely input lines and their positioning relative to the valve in this schematic showing is not significant except that they are properly shown at the top or the bottom of the valve. Diluent is supplied from diluent supply 48 through valve 24 for various purposes including the filling of the 10 milliliter and 25 milliliter syringes 50 and 52, respectively. Diluted red blood test samples are collected and mixed in red blood count container 26 and white blood count test samples are collected and mixed in white blood count container 28. Lyse material for the processing of the white blood count is obtained from container 54.

A vacuum pump 56 provides a vacuum for various purposes including to reduce the pressure within internal waste container 58. It will be observed that the vacuum level is sensed by a vacuum sensor 64 which trips an alarm indicator such as a light or buzzer, indicating a problem relating to insufficient vacuum. if the pressure of the vacuum falls to a predetermined level. The vacuum sensor 64 also provides an output to the microprocessor proportional to the vacuum which is compared to a predetermined level by the microprocessor. The microprocessor then controls pump operation as required through buffer 62 to maintain appropriate vacuum level. Where very accurate vacuum level control is needed, vacuum regulator 60 is connected to the system to help smooth out variations that would otherwise occur in vacuum levels. valve V18 to regulator 60 is closed when valves V6a and V6b are opened and V4 is closed to apply pressure to the waste fluid tank 58 to clean it out through valve V6a to waste. At that same time, valve V8 is opened to atmosphere (ATM).

The receptacle 20 receives vacutainers so that they introduce blood into the system. A drain tube is located in the lowest portion of the tubular sidewall to provide a drain into the evacuation tube. The drain tube is connected to a vacuum source at an appropriate time in the sequence determined by the program controller function of the computer.

Pivotally supported on the sidewall of the cup support means, just below the guide tube, is a closure flap preferably spring loaded into a position closing the opening. This closure is pushed aside as the vacutainer is inserted. Separate sensor means detect when a vacutainer is inserted and when removed. The signals from the sensor means may be used to signal the program means to activate the rotary valve 24 to the proper position for receiving a blood sample from the vacutainer and for enabling syringe movement drawing blood from the container.

Similarly, when the vacutainer is withdrawn at the end of the processing, its removal is sensed. The sensory signal, in turn may enable an adjustment of the rotary valve and a reverse flush with the diluent from the syringe 50. This flush will clean out the blood from the hypodermic needle. The stream of diluent will be deflected by the closed flap, captured in the gutter and evacuated by evacuation tube.

Considering now the aspirator structure, the aspirator tip 22 is supported on the housing and connected by tubing to the rotary valve 24 as schematically shown in FIG. 2. The aspirator tip 22 is supported to protrude downwardly and out of an alcove. The aspirator is thus positioned so that a beaker or other blood containing vessel can be held under it. A cover is provided with spring means which tends to move the cover into closed position. The cover supports an enclosure in the form of a portion of truncated cone enclosing the aspirator tip 22 in the closed position of the cover. The cover is open to enable placement of a blood sample container under the aspirator tip. When the container is removed, the cover can be manually returned about its pivot means to its closed position. Sensor means detect a closed condition of the cover to activate the rotary valve to a position to provide cleaning fluid to the aspirator tip 22. After the container is removed, and presumably the outside of the aspirator tip wiped clean, the closure can be moved by the handle to closed position wherein diluent from syringe 50 is forced through the aspirator to clean it. The tip enclosure provides a liquid collecting basin which directs the cleansing solution into a drain.

As seen in FIG. 1, on the opposite sides of the intake are the red blood cell receptacle 26 and the white blood cell receptacle 28. These containers in the system are designed to be filled automatically and simultaneously. It is possible, however, for containers 26 and/or 28 to be filled manually with properly diluted solutions of a given sample and tests performed on those solutions. Instead of processing the whole series of tests manually or automatically, the processing may be limited to partial or full test for either or both the red or the white cells. Alternatively, the system in some embodiments can take a manual dilution for a white cell count, and automatically draw off and perform the further dilution for a red blood count depending on its program capabilities.

Whether filled automatically or manually, the blood collected in containers 26 or 28 is then processed through passage of 138 or 140 in the bottom of the container. Advantageously, containers 26 and 28 are formed in clear, transparent blocks through which passage 138 and 140 are bored. Passage 138 is, in turn, connected to a tubular passage 34 in block 36 by means of a hose which connects conveniently to coupling 142 in the block. Similarly, passage 140 connects to a similar hose connection to passage 41 in block 42. Passage 34 is arranged to pass tangentially by the jewel orifice 146 (FIG. 2) pressed into the tube 38. Orifice 146 is schematically represented in FIG. 2 and an orifice 148 for the white blood cell processing is similarly represented in FIG. 2. On opposite sides of the orifice 146 are electrodes used in the pulse counting technique conventionally used in blood counting apparatus and broadly described, for example, in U.S. Pat. No. 3,921,066 of Angel Engineering Corporation. Specifically in each passage 34 and 41, there is provided an electrode which is placed along the periphery of the bore and connected by suitable electrical connection to a source of potential and the counting circuit. Inside tube 38 of insulating material is a larger electrode connected by a suitable electrical lead into the counting circuit.

It will be understood that the white blood cell count structure employing insulating tube 44 surrounded by block 42 containing passage 41 is similar to the red blood cell count structure except that orifice size is different and appropriate to the cells being counted.

Now considering the rotary valve 24 seen in FIG. 1 and schematically in FIG. 2, it will be appreciated that the valve is composed of three cylindrical blocks 162, 164 and 166, sometimes called discs, with the middle block or disc 164 rotatable about the spindle 168. It will be understood that each of the discs has ports through it. The ports in discs 162 and 166 are located in positions essentially corresponding to one another. Thus, they are axially aligned at all times However, the ports in movable disc 164 are moved from one position to another in order to effect different combinations of connections as illustrated in FIGS. 3a, 3b, 3c and 3d to be discussed hereafter.

Preferably, the spindle of the rotational valve is a tube provided with a hose 194 (FIG. 1) connecting it to a supply of cleaning solution to clean the surfaces between the discs. Means is provided to separate the discs and ports are provided in position to line up with the spacing between discs 164 and 166 and with the spacing between discs 162 and 164, respectively, in the open position. While cleaning may be done manually and step by step as described in application Ser. No. 675,378, the means provided may be automatic and thus under command of a processing program.

The upper and the lower discs 162 and 166 are provided with similar ports. Disc 162 has ports labeled A through H. Similarly, disc 166 has ports A' through H' in the same relative positions so that as aligned by key post 163, correspondingly lettered ports of disc 166 will be axially aligned with those of disc 162. The middle movable disc 164, however, has a different pattern of ports J through M which cooperate with the aligned ports in the other discs to perform different functions in the different positions of disc 164. In general, and contrary to the suggestion of the schematic line drawings of FIG. 3, in practice, the ports in the middle disc have been somewhat smaller in diameter than those in the outer discs. Additionally, each of the discs has double ports D, J and D', which, at least in one situation (FIG. 3b), are aligned. The two ports in disc 164 are together called J, but the smaller of the two is the port which performs the blood sample measuring function for red blood cell analysis, and only that smaller port is filled with blood sample. Both the smaller port of double port J and the single white cell test port K are intended for measurements of highly repeatable volumes.

The ports J and K need not be precision formed since they may be calibrated in the equipment, but they must be stable in volume and not be subject to change in the normal use of the valve. The larger single hole is used in the white blood cell count since the amount of dilution required in the white blood count is relatively smaller than in the red blood count. In connection with the red blood count, the smaller of the pair of holes marked J is the one which is filled with the sample. In order to provide the selected amount of diluent required for the red blood count in a reasonable period of time, the larger parallel hole is provided and diluent is fed in parallel through both holes. Thereby, while the sample is being washed out of the small hole by some of the diluent, an additional greater volume of diluent will pass through the larger hole. The parallel paths enable enough diluent to pass through the valve 24 in the limited test time allowed for that valve position.

The various indexed valve positions assumed in operation have been shown highly diagramatically in FIGS. 3a, 3b, 3c and 3d. It will be understood that in these diagrams, only those lines connecting the operative ports in a given position have been shown for clarity.

Figure 3A:
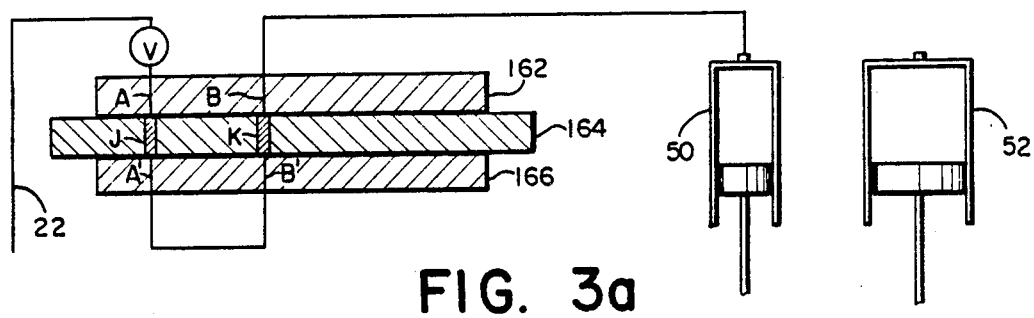
FIGS. 3a, 3b, 3c and 3d are sequential schematic views intended to show fluid flow paths through the rotary valve in successive positions.

FIG. 3a shows the rotary valve position in which aspiration is occurring and the metering holes K and the smaller of the pair J, are filled in series. This is accomplished by connecting the aspirator tip 22 in series through ports A, J, A', B', K, B and into the syringe 50 as the plunger of that syringe 50 is withdrawn to draw the blood sample toward it.

Figure 3B:
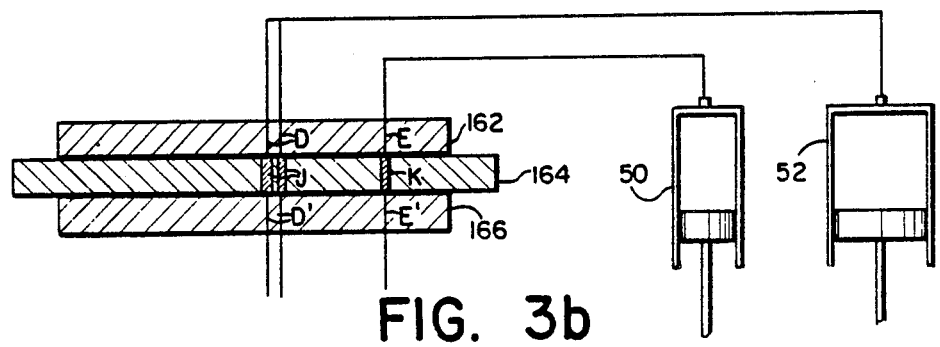

FIG. 3b shows the valve position for dilution wherein the larger syringe 52 filled with diluent is emptied through both of the ports J in parallel, the smaller port containing the blood and the larger port without blood. The double ports J are in series with the corresponding double ports D and D' in discs 162 and 166. Referring to FIG. 2, the larger syringe 52 empties through the double ports, including the smaller port containing the small measured blood sample into the red blood count container 26. At the same time, the smaller syringe 50 empties through the port K filled with a larger measured quantity of blood, entering through port E and exiting port E' to place the mixture in the white blood cell count container 28.

Figure 3C:
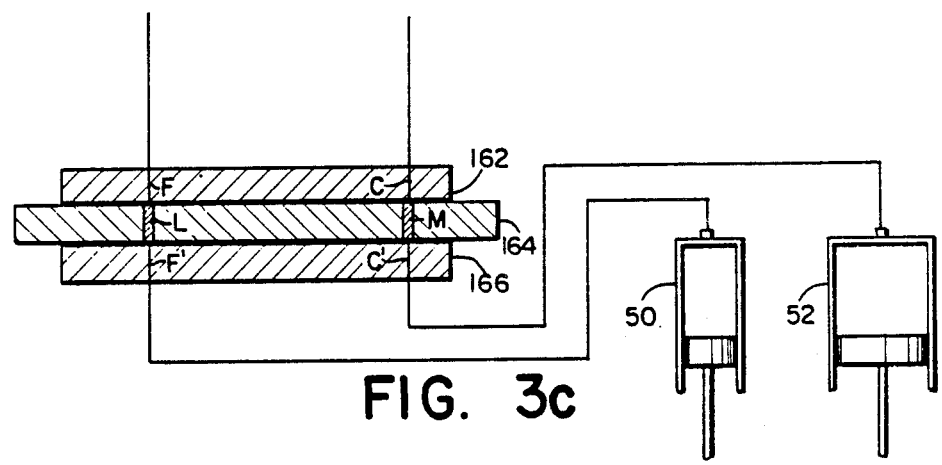

FIG. 3c shows the rotary valve position in which the syringes 50 and 52 are charged from the diluent supply 48. This is done bringing a line through ports F, L and F' to syringe 50 and through ports C, M and C' to syringe 52.

Figure 3D:
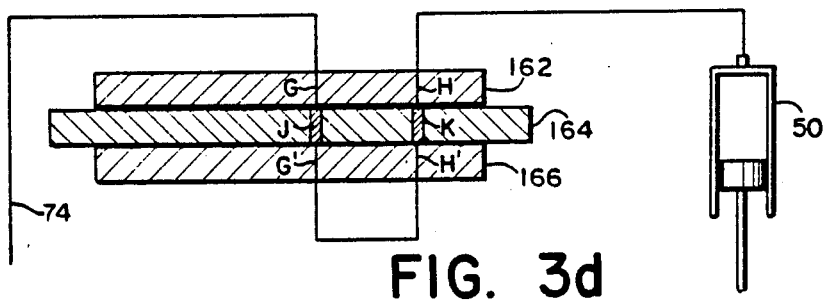

FIG. 3d is the alternative position to the valve for aspirating blood from a vacutainer source. As in FIG. 3a, only the smaller of the J ports in disc 164 is filled in series with the larger K port in disc 164 by drawing fluid into syringe 50. This occurs in series through port G, smaller port J, port G', then, back through port H', red cell metering port K and port H to syringe 50.

While the valve 24 herein has been shown and described as a particular type of rotary valve, it will be clear to those skilled in the art that many changes can be made in the rotary valve as shown or that a linearly sliding valve or other equivalent can be substituted for the purpose of this invention.

Referring now to FIG. 2, the overall operation of the fluid system will now be described. As will be described, the apparatus described thus far, plus other devices and mechanisms shown schematically in FIG. 2, are automatically controlled by the microprocessor computer system illustrated in FIG. 4. Sensed signals detecting key parts of the process are fed to the microprocessor to initiate, terminate or otherwise cue action provided by the program for automatic operation of the system. The microprocessor is contained within housing 10 using the input controls 16, seen in FIG. 1.

To begin the process, diluent is drawn from supply 48 by opening solenoid valve V17. In order to know the amount of diluent drawn into or dispensed, sensors 234 and 236 are mounted on the housing of the syringes 50 and 52, respectively, in each case to determine a "home" reference position and to enable digital counting of predetermined volume units of diluent drawn into or dispensed from the syringe in response to controlled rotation of a drive motor. After positioning rotary valve in the position shown in FIG. 3c, diluent fluid is then drawn into the syringes to essentially fill them. As a practical matter, the syringes are motor driven. Drive is preferably done positively, such as by providing a lead screw along the plunger handle of each syringe. A drive nut 238 may be driven in either direction by motor 240 to move the plunger of syringe 50 upon command. A drive nut 242 is similarly driven by motor 244 to move the plunger of larger syringe 52. In each case, the motor may be provided with a hollow shaft sufficiently large to allow the lead screw to pass through the shaft along the axis of its motor with the drive nut affixed axially to the shaft.

With diluent in the syringes, the apparatus is ready to work and a blood sample may be drawn through the aspirator tip 22 from an open container by repositioning the rotary valve 24 to the position of FIG. 3a or from a vacuum container by repositioning the rotary valve to the position of FIG. 3d upon inserting the vacutainer into receptacle 20. In order to aspirate, vacuum is drawn by further withdrawal of the plunger of syringe 50, as illustrated in FIGS. 3a or 3d. Either way, a sample is drawn into the smaller measuring bore of the pair of bores J and the large measuring bore K in disc 164. The sample is retained within those bores as the disc 164 is rotated to the position of FIG. 3b. A measured amount of diluent from syringe 50 is fed through bore K to wash out the measured volume of blood sample in the larger hole into the white blood count container 28 and provide sufficient diluent for the white blood cell test. At the same time, the measured proper amount of diluent from syringe 52 is fed through both of the two bores J to wash out the measured volume of blood sample therein and mix it with the proper amount of diluent in the red blood count container 26. At this point, the normally closed valve V14 is opened for a very short measured time, on the order of one and a half second, to add the required amount of lyse from container 54 to dissolve red cells and release their contained hemoglobin. This occurs under pressure applied from pump 56.

Valves V3 and V9 which, like many of the valves of the system, are preferably pinch valve members located to pinch flexible hose portions of the line along which they are interposed. Opening normally closed valve V3 draws red blood count mixture into tube 34 past jewel orifice 146 due to the presence of a vacuum in an internal waste tank 58. Similarly, opening normally closed valve V9 draws white blood count mixture from container 28 through the tube 40 past jewel orifice 148 due to the presence of the vacuum in internal waste chamber 58.

After samples have been moved into the lines respectively passing jewel orifice 146 and 148 by opening valves V3 and V9, valve V5 is then opened briefly to interject an air bubble from 218 and 220 into each of the lines 138' and 140' from each of the red and white blood counting chambers 26 and 28. This opening is for a very short period just long enough for air from pump 56 to form a discontinuity in the diluted blood sample. Valves V3 and V9 are then closed and valves V11 and V12 are opened to draw the respective blood samples through jewel orifices 146 and 148, respectively, due to the vacuum in the internal waste tank 58. The bubble interposed in the line forms a visible, or otherwise sensible, discontinuity, which may be sensed as it passes a sensor along or in the line. Passage of the bubble between two sensing points along lines 138' or 140' represents the passage of an equivalent volume of the blood sample through the orifice to fluid volume contained in that line between the sensing points. Transparent tubing 138' may be employed between the red blood container 26 and the jewel 146, and similar transparent tubing 140' between white blood container 128 and jewel 148.

Such photosensors as seen in FIG. 2 are placed at the beginning and end of a measured length of the respective lines 138' and 140'. Discontinuities in the lines are sensed to respectively start and terminate the count of the counter thus, applying the count to a known measured volume in each case. Sensors 222 along line 138' initiate such counting for the red blood count, and sensors 224 along line 140' initiate the counting for the white blood count. Sensors 226 along line 138' terminate the red blood count and sensors 228 along line 140' terminate the white blood count.

An HGB measurement is made while the sample is still in the white blood container 28 using the light source 230, and the HGB detector (photodiode) 230b.

Also, just before counting begins on the red blood count side, valve V17 is opened together with valve V15 and valve V11 to waste 58 to supply diluent, which is advantageously also an electrolyte solution, at a high rate to prime and fill from the back or internal side of jewel orifice 146. During counting, valve V15 is closed but valve V13 is opened to cause a reduced flow of cleaning diluent through choke 232 past jewel orifice 146 to sweep away red blood cells to avoid recounting of those particles which otherwise might produce error due to their swirl around electrode 152 in tube 38.

Once the count is completed, the sample can be fully evacuated from the container 26 and 28 by opening valves V3 and V9.

The rotary valve 24 is then placed in the position of FIG. 3b, and clean diluent is passed through the measuring orifices and into the red and white blood count containers 26 and 28 to rinse them. Then, containers 26 and 28 are evacuated through valves V3 and V9 to internal waste 58.

The system can be designed so that the tubes normally containing fluid are kept wet by arranging the timing of evacuation to occur just before the new sample is introduced.

The system of the present invention makes possible completely automatic cycling which is programmed for computer control. Such programming enabling complete automation and rapid throughput through the device is made possible not only by the described features of the present invention but by the control system which will now be described.

The processes described are controlled by a microprocessor and associated system as shown in FIG. 4. The microprocessor 250 is provided with a keyboard input 16, as seen in FIG. 1 and in greater detail in FIG. 5, and may be supplied with a differential keyboard input 17 as well. Alternative outputs may be provided by way of display device 18 which may be a cathode ray tube or other type of alpha numeric display and optionally by a printer 252 which prints hard copy 14 as illustrated in FIG. 1. One of the major functions of the microprocessor is to provide programmed control of the steps of operation as described in connection with FIG. 2. There may be many kinds of controls involved, and these are lumped together and represented as a single box 254 labeled multiple system controls, most of which have feedback to the microprocessor of some sort, either from the controls or from means monitoring the device operated by the controls. In addition, there is a system calibration system 256 which, in this representation, also includes a security system (not separately represented). Additionally, there are system alarms 258, which, in some cases, may be local and self-operating and, in other cases, feed through the microprocessor to generate a message on the display and may actually be fed back out to some sort of annunciator system.

Particularly, the calibration and the security systems require memory 260, and other aspects of the system controls may require instructional memory as well. Memory here is represented as a simple in/out representation but could take the form of one or more types of memory for the various memory functions.

In order to make the microprocessor responsive to input from a remote processor or input terminal 262, a modem 264 is ordinarily provided enabling transmission of messages over telephone lines by microwave or otherwise, as is widely known and understood in the art. Alternatively, other system matching communication links 266 such as RS-232 may be used or two or more systems may be used in parallel or to different remote locations.

A computer interface option is possible. Messages can be transmitted to a computer automatically at the end of a test or by operator command. A preferred interface is capable of bidirectional transfers.

The printer 252 is also an option which may not be needed by every user. The printer will provide a hardcopy fanfold or single ticket with the date, time, patient identification number with the corresponding data including the platelet histogram.

Figure 5:
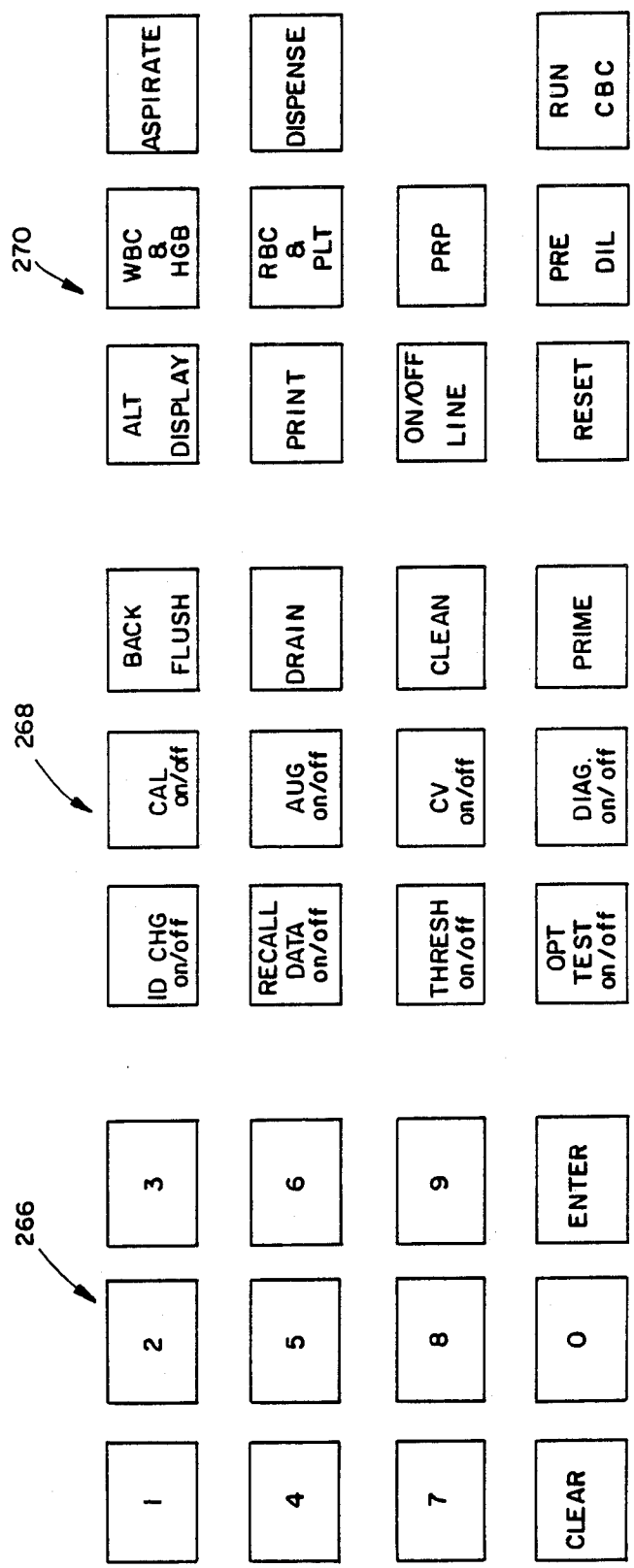
FIG. 5 is a representation of keyboard layout of the keyboard shown in FIG. 1.

Referring to FIG. 5, the keyboard includes a panel 266 of numeric touch keys, which might also include control panels 268 and 270 providing keys to control various system function as suggested by legends on the keys. Some of the functions may alternatively be automatically controlled by the system in accordance with a preset program in memory, as well as being manually accessed and initiated through the input selection keys.

A differential count keyboard option is also available using plug in module 15 seen in FIG. 1. The differential keyboard 17 will enable the operator to enter the differential count. If CBC data is present in the system, it will be matched by I.D. number and printed automatically when the differential is run. The differential may also be printed without running a sample on the instrument by entering the appropriate I.D. number and manually selecting print. All data present under this I.D. number will then be printed. If the WBC count is available, the differential counter will print the absolute white counts as well as the data and differential.

Figure 6:
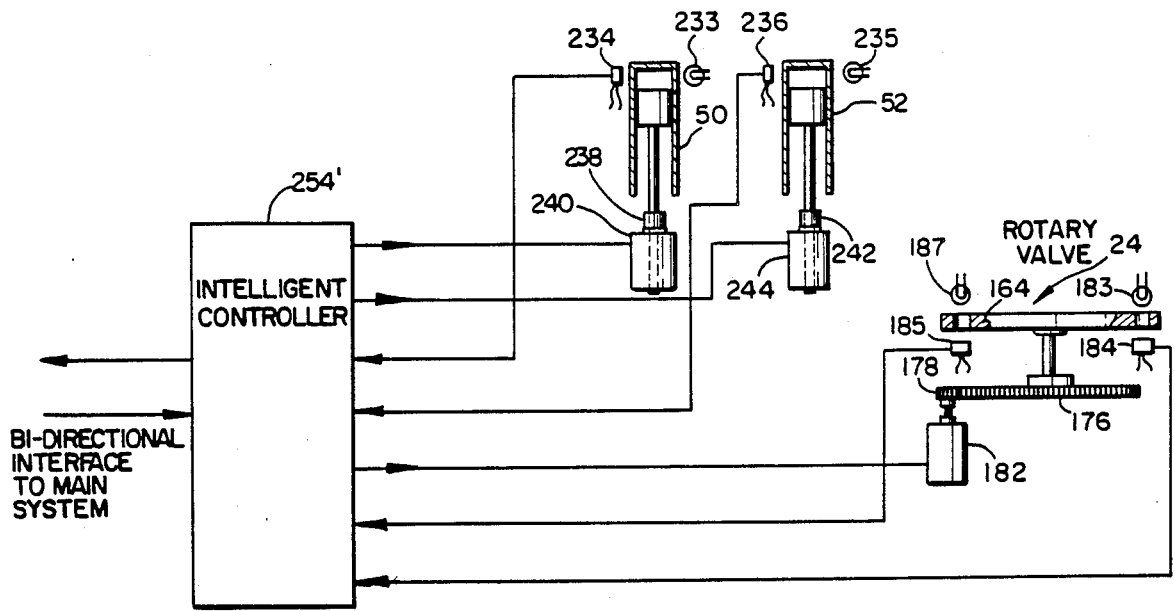
FIG. 6 is a block diagram showing schematically drive motor controls for motor driven parts of the system.

Part of the multiple system controls involves a so-called intelligent controller 254'. Intelligent controller 254' as seen in FIG. 6 effectively controls the stepping motors 240 and 244 driving the syringes 50 and 52, respectively, and the stepping motor 182 driving the movable disc 164 of rotary valve 24. In accordance with the present invention, not only is the program for moving the syringes provided to accomplish each of the steps in the preset cycle but positioning is sensed and fed back to the intelligent controller so that the motor may be placed at a "home" position at least once each cycle. Thus, the stepping motor moves stepwise from one programmed position to another, its stopping point being determined by the direction and number of pulses fed to the stepping motor to drive the syringe or the rotary valve from one predetermined position to another.

Considering syringe 50 for example, the fluid in the syringe may be monitored by a sensor 234 receiving light from a light source 233 so that when the plunger occludes the light, a step or pulse in the sensed output at sensor 234 will occur, indicatinq that the syringe has reached home position. The home position, however selected, is such that, for example, the syringe may have been filled to an opereating level and may aspirate further to draw blood into the system through the valve. The amount of movement required to do this is carefully predetermined and the number of steps required of the stepping motor 240 driving nut to move the lag thread on the plunger will be repeated from one cycle to another. When valve position is changed, the plunger and syringe 50 may again be moved to discharge fluid through a different line to discharge the white blood cell sample into the container 28. Thereafter, the valve is repositioned so that further discharge of the diluent fluid from syringe 50 will clean either the aspirator tip or the vacutainer compartment as previously described. Finally, as the valve is repositioned to still another position, the syringe is moved back toward home so as to aspirate a predetermined amount of diluent into the system and be ready for another cycle.

The syringe 52 operates in exactly the same way, driven by stepping motor 244 through drive nut 242. "Home" is detected in this case using light source 235 and detector 236 through the plunger.

In connection with the rotary valve, the movable disc 164 moves to a different position in accordance with the program. Whether the blood is fed in through the aspirator tip or from a vacutainer, sensing means will detect the presence of a container and initiate a proper program of valve positions, including one for aspiration from that container. However, only one position, for example, the position in which the syringes are filled, may be selected as the home position. In this case, the disc 164 which may be provided by perforations through its outer, larger diameter edge, or by another system which employs a light source and a home detector sensor 184 to indicate when home position is reached. In that case, the alignment of the hole with the light on one side and the sensor on the other will indicate that the position has been reached. As a practical matter, refinements are provided whereby as the change takes place from non-illuminated to illuminated, home is recorded as being achieved. Home is always approached from the same direction so that a program may provide for by passing the hole so that it may be sensed on reversing the direction of movement from the proper side.

Once home has been recorded, then the motor 182 drives gear 178 to move gear 176 associated with the movable disc 164 to know predetermined positions by taking a predetermined number of steps in a predetermind direction for each move. The showing in this drawing is schematic and quite different from the showing in application Ser. No. 675,378 which merely shows the scope of the concept. However, a program may be derived mathematically for moving the valve from one operable position to another and when the number of steps and direction of each move is fixed, providing this information in memory enabling repeating the direction and steps required starting from home on each cycle in response to the proper sensed condition to proceed.

A typical stepping motor drive moves effectively in half steps, where a half step is equal to 0.1 degree of rotation. Thus, for 180 half steps or 90 full steps, 18 degrees of rotation will occur. The valve may be set, for example, to rotate 18 degrees, then 36 degrees, and movements are on this order of magnitude rather than a full rotation or even a half rotation.

Various test procedures may also be incorporated for periodic check of accuracy. For example, an algorithm may be provided to make sure that, after a predetermined number of steps, the home detector 184 senses no light. If it does, the drive has not worked and drive failure is reported at the output. However, assuming the drive works properly in the proper position, detector 185 should then sense light from source 187 through another hole in disc 164. If light is not sensed by either when the movable disc is in the position where detector 185 should sense light, then a problem exists, such as proper drive is not occurring. The program should then call for a reverse drive and repositioning at home. If a repeat of the test again shows improper positioning, the display should print out the nature of the misfunction. If the device performs properly, it should proceed. Another test for proper operation is to cancel a sequence if the position sensor 185 provides no signal when the rotatable disc 164 is in an operating position. In that case, the valve should be returned to home and the sequence repeated with the same sample. Again, if the proper positioning is not obtained, the output display 18 should carry a message indicating the type of misfunction.

Backlash is always a concern as a source of error. Techniques to minimize backlash during automatic or manual processing are built into the programming for the instrument of the present invention. For example, in charging a syringe, the program may be designed to slightly overfill the syringe so that the fluid level goes back beyond standby. Then, in order to set the syringe at the standby position, in which the syringe is fully charged, the plunger must be moved in a direction to discharge part of the fluid back into the reservoir. The same kind of technique is provided with the rotary valve and in all of the systems the approach to home is always the same direction so that backlash does not cause an error.

Figure 7:
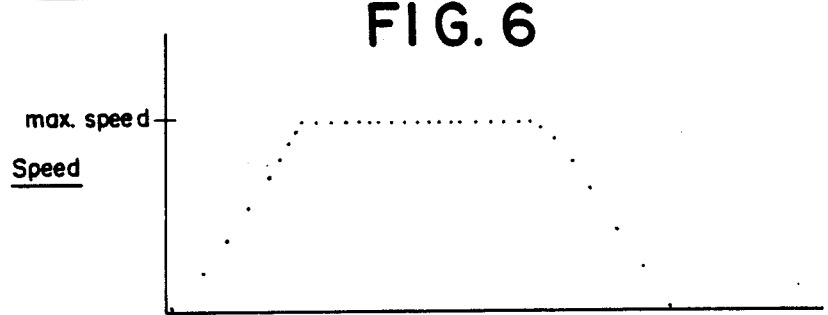
FIG. 7 is a plot of stepper motor speed versus time.

Another technique that is followed in connection with the use of the intelligent controller in driving the stepping motors is to accelerate the motor slowly when starting and then decelerate the motor slowly as the end of the particular segment of movement is reached. The number of steps is preprogrammed so that this is a very reliable technique to prevent fluid surges and overshooting by the driven component. As seen in FIG. 7, the pulses are initially spaced further apart and increased in frequency at such a rate as to permit linear increase of speed during acceleration, and the techniques reversed for deceleration. At maximum speed, the pulses are uniformly spaced. One reason for this precaution is to move the blood without breaking up the liquid to air interfaces. The profile seen in FIG. 7 can be applied to the stepper motor using the intelligent controller and thus efficiently and relatively rapidly accomplished the movement of the controlled element from one position to another without causing shock or damage to the blood cells, or otherwise disrupting the tests or overshooting positions.

The automatic programming through the microprocessor speeds routine cleaning functions. An automatic cleaning cycle is provided to clean the valve after each use and to clean the aspirator tip and the vacutainer input.

Calibration is perhaps the function most vital to the operation of the device. Calibration has to do with standardizing the instrument to known correct values. This is done by providing manipulation, changing results to provide a calibration factor or multiplier which corrects the respective counts. Common to the various calibration techniques described hereafter is the storage of calibration parameters in memory, although calibration can be taken away from the instrument computer, and done manually or by remote computer.

The instrument may be calibrated by using a standard calibration sample and calibrating to the assayed values, or the calibration factors may be adjusted directly using the keyboard input.

One method of calibration is calibration with averages. The operator is able to use up to 100 tests, to calibrate the instrument. The microprocessor is programmed to automatically calculate the averages and the percentage coefficient of variation (Cv %). The computer may compare automatically readings taken within a range of acceptable values. The computer can manipulate and edit data for quality assurance. Such automatic calculation reduces the errors caused by calibrating to a small data base and eliminates time consuming calculations.

The instrument may be programmed to recalibrate itself in accordance with averages taken from repeated tests. Alternatively, the operator can modify data according to his own version. It is also possible to literally manually change the calibration to any values. It is preferably required to input a security code at the keyboard 16 before the microprocessor will permit access enabling modification of the calibration. If desired, a security code may be required for access to other information, including test data, stored in memory, as well.

For any sensitive operations, the program may require that a security code may be entered so that access may be limited to cleared supervisory personnel. By controlling the number of people who can adjust the threshold or calibration values, chances are lessened that these values will be casually or inadvertently adjusted or tampered with.

The security code may be a three digit code. Without use of the security code, the display will allow the count and the calibration factor to be viewed but not changed by an operator. Once that code is placed in the system at the proper time, access can be had to the calibration factor adjustment. Calibration may then be displayed in terms of the correction factor for each of the successive readings. A change may be made manually or automatically, for example, by using the results from other machines for a given sample or automatically by using averages of various samples. For example, a change can be cross-checked on different instruments to see whether results are consistent and adjustment made if results are not consistent. Checking on a single instrument using multiple samples and rejecting patterns deviating from a stated norm is another calibration technique which may prove satisfactory. For example, one way of handling calibration is to take the historical average of up to 100 recent tests which may be stored in memory. Either way, what is derived is a calibration factor, a multiplication factor by which the results of the instrument actual cell count are adjusted.

One method of calibration using patient data utilizes memory in an instrument provided with the capability of fully storing the results of the last hundred tests. Provision may be made for discarding those few tests that depart from a preestablished norm and then taking the average of the remaining tests for calibration.

Another method uses multiple run on the same sample. It is important not to have more than two to three percent coefficient of variation (Cv %) error in reproducability on any given set of runs. The average and standard coefficient of variation capability of the instruction can be calculated before proceeding with calibration of the instrument.

To assure maximum statistical accuracy, in addition to calibration of the system, a given sample may be run multiple times: for example, run three times and then the output is taken as the average. Such a multiple run procedure may be part of the program provided the microprocessor in accordance with the present invention. What is developed by way of calibration is a factor by which results may be multiplied to give an actual or final read out.

The instrument also provides what may be termed floating average. It will store all data for up to the last 99 tests. Access to any of these tests may be accomplished using the ID number of a particular test. By using ID numbers for access, any of those tests identified at any time are subject to deletion. It is possible to make substitutions, interchanges, or any other type of computer manipulation among various tests, keeping data of each complete test together. The computer can determine what an average or mean value should be, for example, in accordance with an algorithm and can calculate and apply the standard deviation or coefficient of variation in any other accepted way in order to use the material for future comparison purposes. The instrument also provides for recall of test by ID number, and ID number change. It permits the tests recalled to be modified in their normal sequence position or to be repositioned relative to one another and it permits interleaving of new tests relative to old ones. An ID number change can be made using the security code and, then using the recall, that ID throughout the system can be changed, if desired. The system is designed to recall, make a change and revert back. In accordance with its program, ID number may be accessed automatically through the use of bar codes or other types of automatic reader devices, as well as by key input.

An internal clock provides information on timing and can include the times when calibration occurs and when a test is run. Information on how much calibration was off can also be ascertained. It is even possible on the system to have a Bull algorithm included to aid in calibration.

As the diagram of FIG. 4 suggests, calibration may alternatively be accomplished from a remote processor terminal 262 through the modem 264. The remote processor is capable of remote control of calibration in any number of ways. It can use stored data from the apparatus being calibrated, it can require that apparatus to make specified runs and use that data alone, or in combination with other data, and it can provide the basis from other apparatuses it supervises including an average or use any other source available to the remote computer. The remote terminal also permits remote change of the security number itself or any security controlled information in the apparatus computer by a security code which may be a three digit code. At the remote processor terminal, it is also possible to get data on individual tests by giving the security code and the code number for the individual patient. The data received back typically includes patient data such as average counts, number of samples and information relative to the time of each test and the time between calibrations. Information of the general nature on the microprocessor 250 as a data center, such as the daily value of the control, is also available at the remote terminal.

The instrument can automatically calibrate itself if the automatic-calibration option is selected. The unit will call the factory (via modem) with an internal preset phone number. It will then pass the parameters from the last test run or the averages, over the phone lines to the factory computer. The factory computer may ask for additional control material to be run. The calibration factors are then computed, within the factory computer, and sent back to the instrument. The operator will be informed when the calibration is complete.

Preferably a hard wired modem without accoustical material may be used, such as a Bell 103, or alternatively, a Bell 212. As an option, the modem may be a separate printed circuit card, or alternatively, hard wiring with standard chips to the interface.

Cell sizing is derived from the histograms, providing a more sensitive means of deriving MCV and MPV. Platelet counts are monitored and automatically extended for counts below 40,000 to obtain enough statistical data to acquire the histogram. In rare instances, if macrocytic thrombocytes or microcytic erythrocytes are present, the instrument is capable of performing platelet counts on platelet-rich-plasma.

Figure 8A:
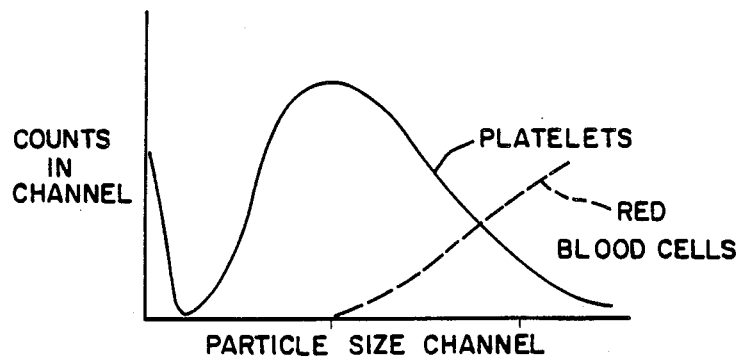
FIGS. 8a, 8b and 8c are plots showing distribution of platelets in a test sample by size, the platelet count versus the logarithm of particle size and the step change of the logarithm scale versus the logarithm of particle size.
Figure 8B:
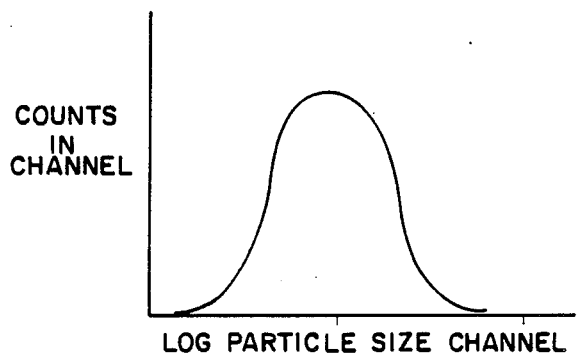
Figure 10:
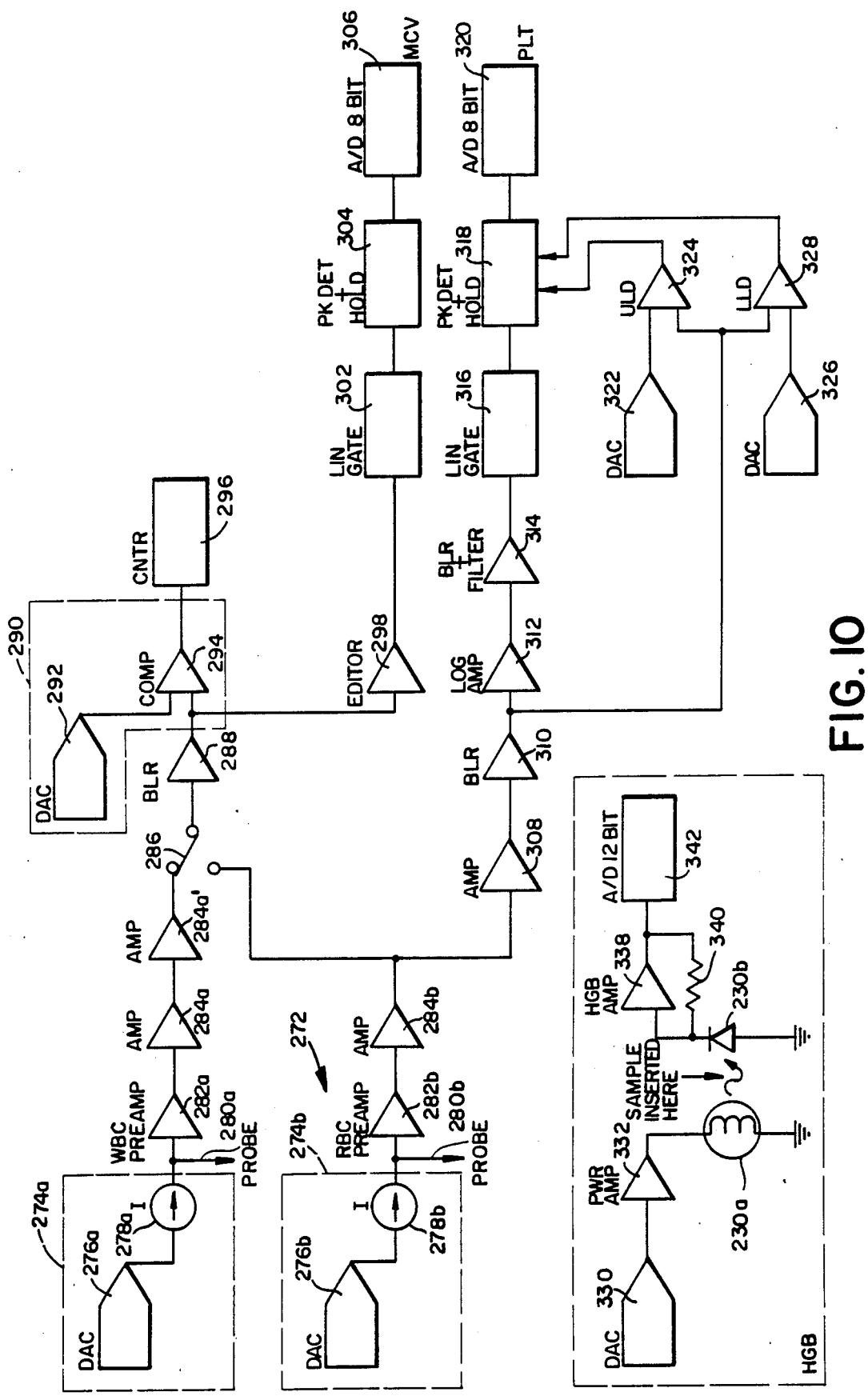
FIG. 10 is a block diagram of an analog circuit for modifying various blood constituent related information.

FIG. 8a shows a typical platelet size distribution curve. Blood particles of all types including platelets are far from uniform in size. In fact, sizes can vary infinitely within a range. Therefore, in making measurements of particles, it is customary to count the particles in a particular "channel" or very limited band of particle sizes and then make similar counts in adjacent bands throughout the selected range to be examined for that particular particle. That is, for example, in examining platelets the channels are indicative of total particles are counted in each of the adjacent channels of platelet size, ranging from smaller to larger along the horizontal axis of the graph. While the example here is of platelet count, it will be understood that similar particle distribution counts can be, and are, made for other blood particles, such as white and red blood cells. The curve on a semi-log axis of platelet size distribution, as seen in FIG. 8b, is generally bell-shaped. For example, semi-log graph may be derived by taking the log of the input amplitude 312 as seen in FIG. 10. Distortions are encountered however, because other particles of small size may occur in large numbers and overwhelm the sizing circuitry. Also, on the higher end, as seen in FIG. 8a, there can be confusion caused by overlap of larger particles in the blood, particularly red blood cells, which are not distinguishable from platelets in the count.

In accordance with the present invention a cut off is made at selected ends of the normal curve for platelets within regions where other particles are not normally detected. Thus, a portion of the curve near the peak and down the slope on each side for a significant distance is taken as defining the shape of the curve. Then, based upon the typical shape of known platelet size distribution curves, the rest of the shape is extrapolated. The number of platelets of each size can be determined by a taking a count from under the extrapolated curve, either total count, or channel by channel. In this way, interference from the small particles at one end and from the large red cells on the other can be ignored.

Figure 8C:
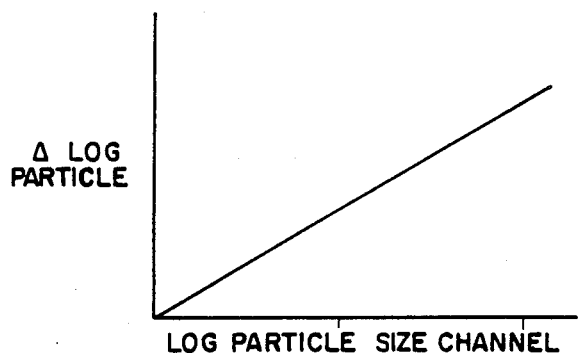

This can be done by plotting the logarithm of the counts in the various channels near the peak to derive a bell-shaped curve as seen in FIG. 8b, instead of the curve of FIG. 8a. The log v. Δ log curve should then provide an approximately straight line. Taking the straight portion of the curve from the peak region to extrapolate upwardly and downwardly by extending the straight line yields the straight line of FIG. 8c as a good approximation. This extrapolation can be done using the least squares fit formula, for example. Then, by reversing the process, the microprocessor can effectively reconstruct a proper curve to represent platelet distribution without noise and red blood cell interference.

It will be understood that in a normal situation the points obtained by taking the log of the counts in the various channels will not fall strictly along a straight line so that it is necessary to use the computer capabilities of the system to find a mean value straight line over a substantial distance and then extrapolate that line from where it begins to curve. Using this straight line technique there has to be some criterion about whether counts are taken or discarded. As a practical technique, the straight line is generated from the peak out in each direction and since the peak has the most accurate information, that portion of the curve is given a weighted reliability. In determining the direction the straight line should take in deciding effectively which points to eliminate. Extreme points can be eliminated on a prearranged discard formula.

In the field, threshold values are subject to variation, like other parameters in blood testing. Changing the threshold values, however, requires access through the security code. These threshold values are particularly important because, in the event that a proper curve cannot be found, the threshold values will determine the platelet count. If the result of the process described is that predetermined criteria of a proper curve are not met, a "no fit" result is generated.

Every effort is made to generate the curve and this is done by using actual points determined by count measurement in the various channels, discarding points that are beyond a certain tolerance, then using the least square fit formula to select the straight line. If the solution simply cannot be found, a "no fit" result is generated and the default procedure takes over using the threshold values given for the platelet count. Some indication on the display or the print out will be given if this has occurred so that the user will be warned that a preset threshold is used.

When the white blood count CBC is complete, a differential count may be made which classifies each type of white cell. This is done with a microscope rather than with the instrument itself. However, the instrument is still of value in that the cell count can be input on the keyboard with the count being made in the conventional way by, for example, counting 100 cells and identifying each type. Effectively the instrument will count 20,000 to 30,000 cells to get a bigger statistical base with better accuracy and will sort and match the counts. Referring to FIG. 1, the differential values can be entered on the keys 17 of the hand held unit 15 designed to be plugged into the instrument and preferably on a sufficiently long connection cord for facilitating use at a remote position. Nevertheless, even with the larger cell count by instrument, the actual count is still made from the slide. The percentage is still the same but the absolute numbers for the volume is much improved. Also, seeing white cell ratios ahead alerts the operator to a possible problem.

FIG. 9 shows a preferred format for information that is printed out on a ticket showing blood test results. In addition to test information, the date and time are indicated by the internal clock. A print out of the distribution of platelets is shown.

Values out of the expected range are automatically flagged on the printout card. Each user may define his own expected values or use the default values.

Platelet (PLT) lower and upper valley alarms will indicate that the platelet histogram is out of normal at one extreme or the other of the bell curve. This allows the operator to double check the validity of the results.

It should be noted that the printer can also be used to print out various other selected convenient formats of data. For example, a calibration format prints out adjusted calibration factors. Calibration can also be printed out with averages. Self test results can be printed out as well. Also, there can be a print out of critical volume percentages of each count. There are numerous other types of printouts relating to all aspects of testing and using the instrument.

Referring to FIG. 10, various circuits for making analog adjustments to counts are schematically illustrated in block diagram form. Parallel input circuits are provided for white blood count and red blood count beginning with a programmable current source 274a for the white blood count and 274b for the red blood count. Theae programmable current sources include a digital to analog converter (DAC) 276a for white and 276b for red blood cell circuits. The DACs regulate current sources 278a and 278b, respectively, to give a variable current output which may be manually or computer regulated. An actual white blood count and red blood count are input, respectively, to probes 280a and 280b. The counter pulse modulated signals are fed through preamplifiers 282a and 282b, respectively, and then through amplifiers 284a and 284b. White blood cell count is here fed through an extra amplifier 284a' as well. The amount of amplification, of course, is a design consideration. The position of switch 286 determines whether the white or the red blood count signals will be fed to the base line restorer 288. The output of base line restorer 288 is divided and fed to input amplifier to the differential comparator 294. Comparator 294 is part of a programmable threshold 290. The control of the programmable threshold is digital to analog converter 292 which may be manually or computer controlled to respond to predetermined criteria to shift the count spectrum of the output to counter 296.

It will be appreciated by those skilled in the art that the circuit described thus far concerns counting of alternatively white blood cells and red blood cells. In the prior art, both the current source and the threshold for counting has been fixed. In accordance with the present invention with the circuit provided, the current source and the threshold for counting may each be adjusted under the control of the system computer. This adjustment permits the considered count spectrum to be shifted to whatever proves to be the optimum operating region. For example, if particles are small, the current may be increased and the threshold adjusted to compensate.

The mean corpuscular volume count (MCV) is obtained for red or white count, depending upon position of switch 286, by taking the output of the base line restorer (BLR) 288 as the input of an editor amplifier 298. This, in turn, is processed through the linear gate 302 which feeds peak detector 304, a device which not only detects the peak or maximum but holds that amount until superceded by a greater level. The "mean" is derived by the system computer using an algorithm from the retained peak amounts which are successively output to analog to digital eight bit converter which feeds the computer.

Means is provided to assure that red and white cell counts are given adequate consideration. For example, switch 286 may be such a means which in practice may be an automatically operated device. The red cell sizes are supplied on a time available basis. Since there are many red cells present, only a sampling is necessary to determine the size distribution. The distribution is analyzed by the computer to find the mean corpuscular volume.

Output of the red blood cell amplifier 284b is fed into amplifier 308 of the platelet (PLT) count circuit which is fed through a further base line restorer 310 to a log amplifier 312. Log amplifier 312 provides more gain for the smaller particles to enable better detection. The output, in turn, is fed through a base line restorer (BLR) and filter (314), which may function to eliminate counts which are sufficiently off the curve to be disregarded. The output of the filter 314 is fed to a linear gate 316 which then feeds it to a peak detector and hold device 318 which feeds an analog to digital eight bit analog to digital output 320 which generates the points on the platelet (PLT) curve seen in FIG. 9.

Between the BLR 310 and the log amplifier 312 the count signal is taken off as an input to each of the operational amplifiers serving as upper limit detector (ULD) 324 and lower limit detector (LLD) 328. At the control terminal of the upper limit detector 324 a digital to analog converter (DAC) 322 sets the upper limit of the signal. The DAC 322 is controlled by the program of the computer and the DAC 322 output is fed to the upper limit detector amplifier 324 which also receives the incoming signal from BLR 310. If the threshold set by the digital to analog converter 322 is exceeded, an output is fed to the peak detector 318 to suppress pulses over the upper limit. Similarly, a lower limit detector (LLD) 328 is provided a computer controlled variable lower limit signal by digital to analog converter (DAC) 326, which is fed into the lower limit detector (LLD) 328 along the output signal from BLR 310. If the lower limit is exceeded, an output will occur and be fed to the peak detector 318 to suppress those pulses below the lower limit.

The log amplifier used in the PLT channel provides more gain for the smaller particles, such as platelets, and less gain for the larger ones, such as the red blood cells. This also yields a normal distribution for the platelets as opposed to a log normal distribution.

The platelets upper and lower limit discriminators 324 and 328 are under computer control so that they may be adjusted through the DACs 322 and 326 by computer. Employing these discriminators eliminates from the output effectively useless information in such a way that the computer time is not needed for analyzing useless pulses.

Referring now to the HGB circuit for measuring hemoglobin, an input source digital to analog converter (DAC) 330 supplies a power amplifier 332 with a signal which regulates the intensity of lamp 230a. A sample is inserted between the lamp 230a and photodiode 230b so that different levels of signals for different samples may be compared with the signal level for a colorless fluid standard simialrly inserted. The photodiode output is put through an HGB amplifier 338, in parallel with resistor 340 and the amplifier output is supplied to the 12 bit analog to digital converter 342.

In the prior art use, lamp to photodiode systems have been used for measuring HGB. First, they measure the output of a blank then they measure the output of a sample and they take the difference. The present invention adds a computer in the loop to adjust the lamp output when the standard is present to bring the light output up to a predetermined standard intensity. By making the light output as high as possible, the signal to noise ratio the measurement is improved.

The nature of the computer control in accordance with the present invention has been briefly described. It will be understood that the computer is used in many conventional ways but also in many non-conventional ways in accordance with the present invention. The microprocessor may be programmed to sequence the events, allowing for interruption or alternative actions in accordance with intermediate effects. The microprocessor may be programmed so that when there are problems at a particular juncture some sort of alarm or warning is sounded or shown. If manual steps are required to implement the program, the required manual steps may be requested by a message on the screen provided for in the computer so that the operator will know what to do. Automatic steps may proceed without interference unless there is some problem as detected by various sensed abnormal conditions during tests, as well as by conditions which may be sensed at any time and displayed or which may be used to discontinue the tests and identify on the display the region of malfunction or reason for discontinuance if the problems created necessitate shut down. System alarms may be indicated by a message appearing on the display screen and/or may be indicated by some sort of an audible or visable alarm signal, such as a buzzer or a flashing light. The kind of situation in which a warning light or message should be provided, and interlocks provided to shut down the system, for example, is loss of vacuum in the internal waste tank or exhaustion of the supply of diluent or the supply of lysing fluid or indication of inappropriate pressure, or some lack of function in response to program sequence such as blockage of an orifice.

The program may, for example, on the blockage of an orifice provide its own self-correction effort, such as back flushing the orifice.

If the instrument determines that an aperture is clogged, an attempt will automatically be made to clear the clog and the test will be rerun. An automatic backflush at the jewel orifices of the cell counter at the end of each count is also provided to keep the aperatures free of protein buildup.

In the event that such technique does not work, however, a warning must be displayed and the system shut down.

Examples of a alarms and prompts provided for this instrument include the following:

1. Clog—no counts detected within count time
2. Overrange—if limits within units are exceeded
3. Underrange—if limits within units are not reached
4. Lyse Empty
5. Diluent Empty
6. Waste Full (only if container is used for waste)
7. Platelet lower Valley (excess of noise)
8. Platelet upper Valley (small red cells)
9. Main computer off line
10. Impedence
11. No Fit
12. Time Some of the many diagnostic tests that can be manually run by the operator are as follows:

a. Date and time change
b. Security code change
c. Electronic background test (injecting known signal)
d. Repeat counts of the same dilution
e. Leak test
f. Expected values
g. Sequential number
h. Display check
i. Keyboard check
j. Printer check These tests enable either diagnostic information from the computer to be printed out or result in one of the foregoing alarms and prompts to occur.

Various types of applications of the computer to the present invention have been discussed. It will be understood by those skilled in the art that the techniques described are representative and that many variations are possible as well as other uses of the computer. It is anticipated that other applications for the same computer will be found by those skilled in the art. The claims are intended to include the many variations within the scope and spirit of the present invention.

We claim:

1. The method of determining curve shape in a particular selected blood particle log normal size distribution curve comprising:

analyzing a blood sample using a cell counter to count blood particles within each adjacent channel of blood particle size over at least a predetermined range of particle size, calculating the logarithms of the count of blood particles and the particle size for each particle size channel, enabling plotting of a log count vs. log of blood particle size curve of generally symmetrical bell shape, calculating change of logarithm ($\Delta$log) of counts in adjacent channels, generating a straight line fixed slope plot representing the change of logarithm of counts vs. the log of blood particle size, giving more weight to those points near the peak of the log count vs. log of blood particle size curve in determining said fixed slope line, and reversing the calculation step using the points on the straight line plot and calculating the counts in each channel from $\Delta$log and taking the anti-log of log particle size to regenerate ultimately a new curve showing a redistribution of number of the selected blood particles against particle size.

2. The method of claim 1 in which an average is derived by mathematical manipulation of the regenerated new curve.

3. The method of claim 2 applied to mean platelet volume (MPV) including the additional step of finding from the ultimately regenerated curve the mean platelet volume which is mathematically the average platelet volume.

4. The method of claim 1 in which the particular selected blood particle is platelet.

5. The method of determining curve shape according to claim 1 for calculating mean cell volume (MCV) wherein;

said analyzing step counts red blood cell particles within each adjacent channel, and using the new curve to compute MCV.

6. The method of claim 5 in which the MCV count is computed by integrating or summing up all counts under the new curve.

7. The method of claim 1 in which a mean corpuscular volume count is computed by taking the average of all counts under the regenerated new curve.

8. The method of determining curve shape for red blood count (RBC) in a blood particle normal size distribution curve comprising:

calculating the logarithm and change of logarithm ($\Delta$log) of counts in adjacent channels and generating a straight line plot of $\Delta$log against the log of blood particle size in the channels, giving more weight to those points in channels near the point where the counts in said channels are at a maximum in determining line slope, and reversing the calculating steps using the points on the straight line plot and calculating the counts in the channels from $\Delta$log and taking the anti-log of log particle size in the channels to regenerate ultimately a normal curve showing a redistribution of number of particles against particle size.

9. The method of approximating curve shape in a blood particle log normal size distribution curve comprising:

analyzing a blood sample using a cell counter to count blood particles within each adjacent channel of blood particle size over at least a predetermined range of particle size, calculating the logarithm of the count of blood particles for each particle size channel, enabling plotting a log count vs. log particle size distribution curve of generally symmetrical bell shape, calculating change of logarithm ($\Delta$log) of counts in adjacent channels and the logarithm of blood cell input amplitudes, using the least squares fit formula to generate a straight line representing change of logarithm ($\Delta$log) of counts in adjacent channels vs. the log of cell particle size in said channels, the straightness of which line permits examining the log curve for its uniformity, and determining if the curve does measure up to predetermined minimum requirements, and if not, using measured data to generate the cell count for each cell size between two predetermined threshold limits.

10. The method of claim 9 done by computer, wherein counts are first subjected to a logarithm translation by a log amplifier and standards are stored for comparison together with predetermined tolerances for acceptance and rejection.

11. In a blood cell counting apparatus employing a computer, the method of assuring more accurate results comprising:

analyzing a blood sample using a cell counter to count blood particles within each adjacent channel of blood particle size over at least a predetermined range of particle size, computing a projected count for each particle count channel, making a periodic check of intermediate counts at predetermined intervals during each count to generate periodic results, comparing the periodic results with said projected counts and if any of the intermediate results deviate from the projected count, rerunning the test.

12. In the method of claim 11, employing the following intermediate steps:

following termination of counting, using a program to probe the counting system to determine possible cause of the deviation, and taking corrective action before running the test.

13. The method of claim 11 in which before rerunning the test, the computer makes certain tests of the computer and various instrument locations using built in test capabilities and if the tests indicate correctable problems, connects those problems, but if the tests indicate uncorrectable problems, indicating an error signal.

14. The method of claim 13 in which a table of possible error signals is matched with the error signal and an indicator is selected for activation which identifies the source of the error.

* * * * *

UNITED STATES PATENT AND TRADEMARK OFFICE
CERTIFICATE OF CORRECTION

PATENT NO. : 4,706,207

DATED : November 10, 1987

INVENTOR(S) : James W. Hennessy, Henry R. Angel and Richard A. Carlson

It is certified that error appears in the above-identified patent and that said Letters Patent is hereby corrected as shown below:

Claim 12, line 34, "running" should read --rerunning--.

Claim 13, line 39, "connects" should read --corrects--.

Signed and Sealed this

Fifth Day of September, 1989

Attest:

DONALD J. QUIGG

Attesting Officer

Commissioner of Patents and Trademarks